US009475844B2

(12) United States Patent
Moi et al.

(10) Patent No.: US 9,475,844 B2
(45) Date of Patent: Oct. 25, 2016

(54) METHOD FOR PRODUCING BIO-ACTIVE AGENT FOR THE PREVENTION OF DISEASE CAUSED BY WHITE SPOT SYNDROME BACULOVIRUS COMPLEX AND A BIO-ACTIVE AGENT DERIVED THEREOF

(75) Inventors: Phang Siew Moi, Kuala Lumpur (MY); Gan Sook Yee, Kuala Lumpur (MY); Ung Eng Huan, Sabah (MY); Rofina Yasmin Othman, Kuala Lumpur (MY); Awang Muhammad Sagaf Abu Bakar, Sabah (MY)

(73) Assignee: UNIVERSITI MALAYA, Kuala Lumpur (MY)

( * ) Notice: Subject to any disclaimer, the term of this patent is extended or adjusted under 35 U.S.C. 154(b) by 735 days.

(21) Appl. No.: 13/884,689

(22) PCT Filed: Oct. 31, 2011

(86) PCT No.: PCT/MY2011/000232
§ 371 (c)(1),
(2), (4) Date: Jul. 17, 2013

(87) PCT Pub. No.: WO2012/064181
PCT Pub. Date: May 18, 2012

(65) Prior Publication Data
US 2013/0289242 A1 Oct. 31, 2013

(30) Foreign Application Priority Data
Nov. 10, 2010 (MY) .................. PI2010005260

(51) Int. Cl.
| C07K 14/01 | (2006.01) |
| C12N 15/33 | (2006.01) |
| A61K 35/76 | (2015.01) |
| C07K 14/005 | (2006.01) |
| A61K 39/12 | (2006.01) |
| A61K 38/16 | (2006.01) |

(52) U.S. Cl.
CPC .......... C07K 14/005 (2013.01); A61K 38/162 (2013.01); A61K 39/12 (2013.01)

(58) Field of Classification Search
None
See application file for complete search history.

(56) References Cited

U.S. PATENT DOCUMENTS

| 6,440,466 B1 | 8/2002 | Desai et al. |
| 6,705,556 B2 | 3/2004 | Laramore |
| 6,908,616 B2 | 6/2005 | Vlak et al. |
| 7,323,547 B2 | 1/2008 | Kou et al. |
| 7,749,506 B2 | 7/2010 | van Hulten et al. |
| 2003/0022359 A1* | 1/2003 | Sayre ............... A23K 1/008 435/257.2 |
| 2007/0059808 A1 | 3/2007 | Klimpel |
| 2008/0107652 A1 | 5/2008 | Durvasula et al. |

FOREIGN PATENT DOCUMENTS

| WO | 0109340 | 2/2001 |
| WO | 2004025263 | 3/2004 |
| WO | 2005023992 | 3/2005 |
| WO | 2007083893 | 7/2007 |
| WO | 2008027235 | 3/2008 |

OTHER PUBLICATIONS

Christopher Marlowe A. Caipang et al., "Enhanced survival of shrimp, Penaeus (*Marsupenaeus*) *japonicus* from white spot syndrome disease after oral administration of recombinant VP28 expressed in Brevibacillus brevis," Fish & Shellfish Immunology, 2008, pp. 315-320, vol. 25.

Hugo M. Martinez, "An Efficient Method for Finding DNA Repeats in Molecular Sequences," Nucleic Acids Research, 1983, pp. 4629-4634, vol. 11, No. 13.

Saul B. Needleman et al., "A General Method Applicable to The Search for the Similarities in Amino Acid Sequence of Two Proteins," Journal of Molecular Biology, 1970, pp. 443-453, vol. 48.

H. Wayne Nichols et al., "*Trichosarcina polymorpha* Gen. et Sp. Nov.," Journal of Phycology, 1965, pp. 34-38, vol. 1.

Phang Siew Moi et al., "The University of Malaya Algae Culture Collection (UMACC) and potential applications of a unique Chlorella from the collection," Japanese Journal of Phycology., 2004, pp. 221-224, vol. 52 (Supplement).

Jeroen Witteveldt et al., "Protection of Penaeus monodon against White Spot Syndrome Virus by Oral Vaccination," Journal of Virology, Feb. 2004, pp. 2057-2061, vol. 78, No. 4.

Dae-Hyun Kim et al., "Stable integration and functional expression of flounder growth hormone gene in transformed microalga, *Chlorella ellipsoidea*," Mar. Biotechnol. (NY), 2002, pp. 63-73, vol. 4, No. 1.

Song Qin et al., "Review of genetic engineering of Laminaria japonica (Laminariales, Phaeophyta) in China," Hydrobiologia, 1999, pp. 469-472, vol. 398/399.

Marielle C.W. Van Hulten et al., NCBI GenBank Direct Submission. 28 kDa structural protein VP28 [White spot syndrome virus]. GenBank Acc. No. AAF29807, Feb. 3, 2000.

Marielle C.W. Van Hulten et al., NCBI GenBank Direct Submission. 28 kDa structural protein VP28 (VP28) gene, complete cds. GenBank Acc. No. AF173993, Feb. 3, 2000.

* cited by examiner

*Primary Examiner* — John S Brusca
*Assistant Examiner* — Stephen Uyeno
(74) *Attorney, Agent, or Firm* — Preston Smirman; Smirman IP Law, PLLC

(57) ABSTRACT

A method of producing an agent capable of eliciting immune response against White Spot Syndrome Baculovirus complex in crustaceans of Penaeidae family upon ingestion of the agent comprising the steps of introducing a vector containing genetic sequence of Seq. No 1 into an alga to transform the algae; and cultivating the transformed algae to express modified VP28 peptides according to the genetic sequence of Seq. No. 1 to obtain the agent.

6 Claims, 8 Drawing Sheets

|     |   |   |   |   |   |   |   |   |   |   |   |   |   |   |   |   |   |   |   |   |
|-----|---|---|---|---|---|---|---|---|---|---|---|---|---|---|---|---|---|---|---|---|
| 1   | G | E | L | G | T | A | T | G | S | H | N | T | V | T | K | T | I | E | T | H |
| 21  | T | D | N | I | E | T | N | M | D | E | N | L | R | I | P | V | T | A | E | V |
| 41  | G | S | G | Y | F | K | M | T | D | V | S | F | D | S | D | T | L | G | K | I |
| 61  | K | I | R | N | G | K | S | D | A | Q | M | K | E | E | D | A | D | L | V | I |
| 81  | T | P | V | E | G | R | A | L | E | V | T | V | G | Q | N | L | T | F | E | G |
| 101 | T | F | K | V | W | N | N | T | S | R | K | I | N | I | T | G | M | Q | M | V |
| 121 | P | K | I | N | P | S | K | A | F | V | G | S | S | N | T | S | S | F | T | P |
| 141 | V | S | I | D | E | D | E | V | G | T | F | V | C | G | T | T | F | G | A | P |
| 161 | I | A | A | T | A | G | G | N | L | F | D | M | Y | V | H | V | T | Y | S | G |
| 181 | T | E | T | E | L | Q | T | K | L | A | E | F | E | L | Q | L | L | F |   |   |

Figure 1

```
GGCGAATTGGGTACCGCTACTGGATCCCATAATACTGTTACTAAGACTATTGAAACTCATACTGATAATATTGAA
ACTAATATGGATGAGAACCTCAGAATCCCTGTTACTGCTGAAGTTGGATCTGGATACTTCAAGATGACTGATGTG
TCTTTCGATTCTGATACTCTCGGAAAGATCAAGATCAGAAACGGAAAGTCTGATGCTCAGATGAAGGAAGAGGAT
GCTGATCTCGTTATCACTCCTGTTGAGGGAAGAGCTTTGGAAGTTACTGTGGGACAAAATCTTACTTTCGAGGGA
ACTTTCAAAGTGTGGAACAACACTTCTAGAAAGATCAACATCACTGGAATGCAAATGGTGCCTAAGATCAACCCT
TCTAAGGCTTTCGTTGGTTCTTCTAACACTTCTTCTTTCACACCTGTGTCTATCGATGAGGATGAAGTGGGAACT
TTCGTGTGTGGAACTACTTTCGGTGCTCCTATTGCTGCAACAGCAGGTGGAAACCTCTTCGATATGTACGTGCAC
GTGACTTATTCTGGAACTGAGACTGAGCTGCAGACCAAGCTTGCCGAATTCGAGCTCCAGCTTTTGTTC
```

Figure 2

WSSV3  UT1

Figure 6

```
  1  MDLSFTLSVVSAILAITAVIAVFIVIFRYHNTVTKTIETHTDNIETNMDENLRIPVTAEV

61  GSGYFKMTDVSFDSDTLGKIKIRNGKSDAQMKEEDADLVITPVEGRALEVTVGQNLTFEG

121  TFKVWNNTSRKINITGMQMVPKINPSKAFVGSSNTSSFTPVSIDEDEVGTFVCGTTFGAP

181  IAATAGGNLFDMYVHVTYSGTETE
```

Figure 8

METHOD FOR PRODUCING BIO-ACTIVE AGENT FOR THE PREVENTION OF DISEASE CAUSED BY WHITE SPOT SYNDROME BACULOVIRUS COMPLEX AND A BIO-ACTIVE AGENT DERIVED THEREOF

CROSS-REFERENCE TO RELATED APPLICATION

The instant application is a national phase of PCT International Patent Application Serial No. PCT/MY2011/000232, filed Oct. 31, 2011, pending, and claims priority to Malaysian Patent Application Serial No. PI 2010005260, filed Nov. 10, 2010, pending, the entire specifications of both of which are expressly incorporated herein by reference.

FIELD OF INVENTION

The present invention relates to a method to produce transformed algae bearing antigenic peptides of White Spot Syndrome Baculovirus Complex. More specifically, the host employed in the present invention allows stable transfer of the genetic information and expression of the preferred antigenic peptides over generations of replication.

BACKGROUND OF THE INVENTION

White Spot Syndrome Virus (WSSV) is the infectious agent causing deadly disease in marine crustaceans, particularly prawn or shrimp of the Penaeidae family. WSSV is extremely virulent that prevention and inhibition of its spread in an aquaculture farm seems impossible once settled. The infected prawns have white spots developed on the carapace, appendages and cuticle. Rapid reduction in food consumption among the infected prawns is common phenomenon. The disease can lead up to 100% mortality in a commercial shrimp farm within 7 to 10 days. Researches have been carried out in years to find an effective treatment to cure or prevent the disease. Many of these researches focus on employing the antigenic peptides of the WSSV, particularly envelope protein VP28 and VP19 or nucleocapsid proteins VP26 and VP24, to prophylactically immunize the crustacean against the WSSV infection before the actual infection occurred.

For example, U.S. Pat. No. 7,749,506 describes cloning and expression of different antigenic WSSV proteins in a host cell in order to produce vaccine constituted of the produced antigenic peptides. Another United States patent with publication no. 2008/0107652 discloses development of WSSV's antibody in microalgae *Dunaliella* that the microalgae containing the antibodies is fed to the crustacean to prevent, ameliorate or treat the WSSV disease.

International patent with publication no. 2004083893 provides cell surface expression vector comprising genetic sequence encoding antigen of WSSV and gene of a poly-gamma-glutamate synthetase complex as the expression marker. The vector is hosted in a bacterium for producing the antigen which can be subsequently processed for preparing vaccine or feedstuff additive to prevent or cure the disease.

SUMMARY OF THE INVENTION

The present invention discloses a method of producing a bio-agent for treating, amelioration or prevention of WSSV infection in crustaceans particularly of Penaeidae family. More specifically, the bio-agent is a preferred type of algae hosting genetic information of antigenic peptides of the WSSV and capable of expressing the antigenic peptides undisrupted over generations rendering it an ideal candidate to immunize the crustaceans.

Further object of the described method is to produce a bio-agent containing sufficient antigenic peptides to elicit immune response in the crustacean upon ingestion of the bio-agent. The disclosed method employs a modified genetic sequence which facilitates expression of the antigenic peptides in the bio-agent.

Another object of the disclosed invention is to offer a lasting prophylactic agent for treating WSSV infection that the produced bio-agent can be cultured in a pond together with the crustacean to ensure lasting exposure of the crustaceans to the antigenic peptides.

At least one of the preceding objects is met, in whole or in part, by the present invention, in which one of the embodiments of the present invention is a method of producing an agent capable of eliciting immune response against White Spot Syndrome Baculovirus complex in animal of Penaeidae family upon ingestion of the agent comprising the steps of introducing a vector containing genetic sequence of Seq. No 1 into an alga to transform the algae; and cultivating the transformed algae to express modified VP28 peptides according to the genetic sequence of Seq. No. 1 to obtain the agent.

Preferably, the vector employed in the described method is pSV40 which has shown great stability in the host cell over generation to continuously express the interested modified VP28 peptides of WSSV.

BRIEF DESCRIPTION OF THE DRAWINGS

FIG. 1 shows the peptide sequence Seq No. 1 which is capable of promoting immunity against WSSV infection in the penaeid shrimp upon administration;

FIG. 2 shows one of the possible deoxyribonucleic acid sequences, Seq No. 2, encoding for the peptide sequence Seq No. 1;

Figure 6:
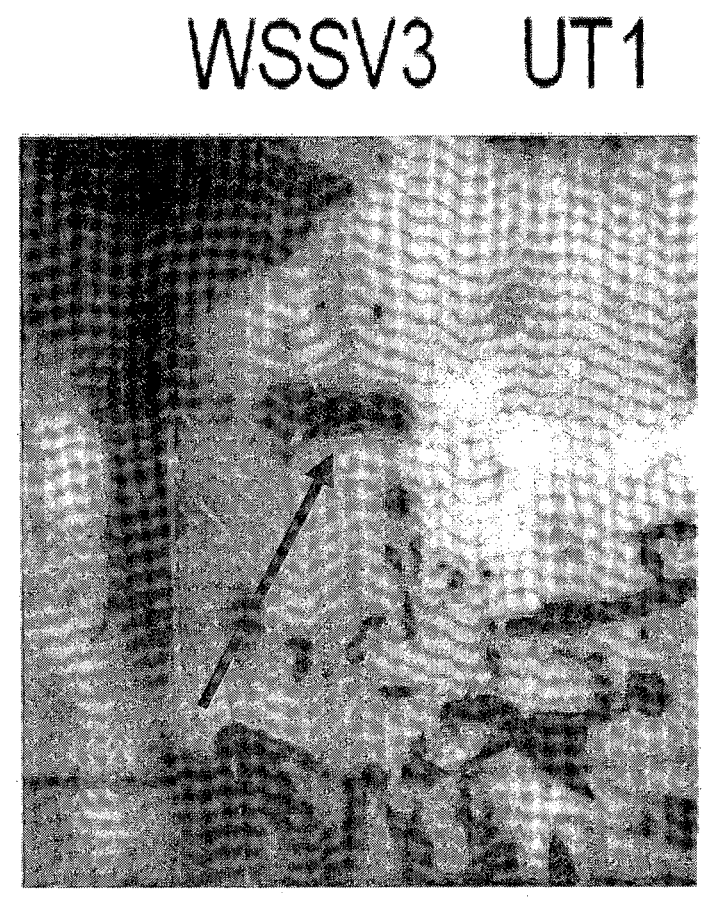

FIG. 6 shows result of Southern blot analysis conducted with the DNA extracted from transformed strain WSSV3 (6$^{th}$ generation) and untransformed strain (UTI, 6$^{th}$ generation) indicating DNA integration;

FIG. 8 shows the native sequence of the VP28 peptide (SEQ ID NO. 7).

DETAILED DESCRIPTION OF THE INVENTION

Figure 3:
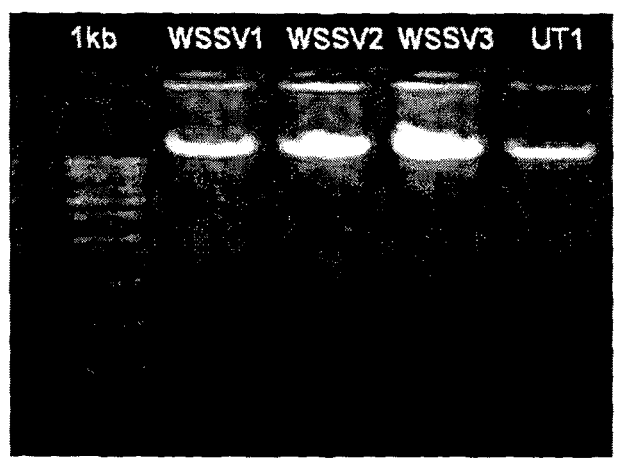
FIG. 3 is a gel picture showing genomic DNA extracted from transformed strains and untransformed strain of *Chlorella* UMACC 001, namely WSSV 1: DNA extracted from transformed *Chlorella* strain 1; WSSV 2: DNA extracted from transformed *Chlorella* strain 2; WSSV 3: DNA extracted from transformed *Chlorella* strain 3; and UT 1: DNA extracted from untransformed *Chlorella* strain 1.

The present disclosure includes as contained in the appended claims, as well as that of the description herein. It is understood that the present disclosure of the preferred form has been made only by way of example and that numerous changes in the details of construction and the combination and arrangements of parts may be resorted to without departing from the scope of the invention.

The present invention includes a method of producing an agent capable of eliciting immune response against White Spot Syndrome Baculovirus complex in crustaceans of Penaeidae family upon ingestion of the agent comprising the steps of introducing a vector containing genetic sequence of Seq. No 1 into an alga to transform the algae; and cultivating the transformed algae to express modified VP28 peptides according to the genetic sequence of Seq. No. 1 to obtain the agent.

In order to express the VP28 peptide and/or its derivatives, the disclosed method transforms the mentioned algae to bear at least one copy of deoxyribonucleic acids (DNA) sequence of Seq No. 1 which encodes for the amino acids sequence of the antigenic VP28. One skilled in the art shall appreciate the fact that a single amino acid can be encoded by multiple deoxyribonucleic acids codon. Thus, the DNA template for expressing the VP28 in the algae may be modified to express similar VP28 peptides via, preferably, slightly different deoxyribonucleic acids sequence which only with at least 70% similarity of Seq No. 1. Moreover, the gene sequence used in the described method of the present invention is modified to achieve better expression rate and stability, yet antigenic property of the modified VP28 peptides is not affected by such modification. Preferably, the expressed modified VP28 peptides is free of the first 29 amino acids at the N-terminal of the original peptides. The removed portion is hydrophobic portion of the peptides. Removal of such portion renders greater hydrophilicity and water solubility to the expressed peptides allowing the produced peptides to be ready for further processed in preparing a WSSV prophylactic agent. For example, the peptides produced within the agent may be extracted to be administered into the aqua farm to immunize or expose the crustacean of Penaeidae family to the antigenic peptides. Thus, resistance against the WSSV in the treated crustaceans is increased through routine exposure to the antigenic peptides. It was found by the inventors of the present invention that continuous exposure to the antigenic peptides in the penaeid shrimps can increase resistance against this viral infection in the shrimp. It is believed the routine exposure allows development of active immunization against the infection. Hydrophobic insoluble substances in aqueous phase tend to accumulate and form aggregates that it limits the exposure of the crustacean of Penaeidae family to the antigenic peptides available.

More preferably, the DNA template of the VP28 to be expressed is incorporated into a suitable vector. To facilitate the expression of the preferred peptides, pSV-beta-galactosidase control vector, but not limited to, is employed in the present invention. The pSV-beta-galactosidase control vector used in the present invention also shows significant stability in the host cell that it is transferred from generation to generation along duplication and capable of expressing the preferred antigenic peptides in the duplicated cells. In order to transform the algae, the introducing step in the disclosed method is performed employing particle bombardment. In more particular, the pSV-beta-galactosidase control vector incorporated with the VP28 modified DNA sequence is delivered via particle bombardment that metal particles such as gold or tungsten are attached to the vector and then propelled into the host cell using biolistic particle delivery system. With the particle bombardment, the host cell, algae, receives one or more copy of the vector equipped with the modified VP28 DNA sequence of Seq No. 1. Preferably, the algae used in disclosed method is *Chlorella vulgaris*. The algae may be of freshwater or marine origin.

Present invention also discloses an agent capable of eliciting immune-response against White Spot Syndrome Baculovirus complex in crustacean of Penaeidae family upon ingestion produced according to the setting forth method. It is known that ingestion of the expressed peptides alone containing the amino acid sequence Seq No. 1 into the penaeid shrimps is not voluntary. Moreover, administration of the antigenic peptides in the aqua farming environment may subject the expressed peptides to potential denaturation thus diminishing its antigenic property upon ingestion. While using the disclosed method to produce the preferred bio-agent, the expressed antigenic peptides are ready to be ingested by the penaeid shrimps together with the algae as algae ingestion is natural behavior of the penaeid shrimps. The algae bearing copies of DNA template for expressing peptides having at least 70% similarity of amino acid sequence Seq No. 1 is a recombinant organism. The produced bio-agent serves as bio-factory platform of the modified VP28 antigenic peptides in the present invention can be mass-produced under specific conditions in the aqua farming environment to serve as a sustainable source of the antigenic peptides to the penaeid shrimps. Providing continuous exposure of the peptides having at least 70% similarity of amino acid sequence Seq No. 1 to penaied shrimps to maintain the immunization against White Spot Syndrome Baculovirus Complex infection. Wrapped within cytoplasm of the algae, the produced antigenic peptides are shield from potential denaturation caused by the water phase in the aqua farm especially fluctuation of pH in water. Besides, algae used as the bio-agent contains various nutrients such as essential amino acids, vitamin B12, beta-carotene, calcium, iron and so on. Thus, ingesting the produced bio-agent carrying the antigenic peptides not only initiates the needed immunization but also promote growth and health of the penaeid shrimps. More preferably, the algae employed for carrying the recombinant DNA and peptides is, but not limited to, *Chlorella vulgaris*. Other algae types may be employed in the present invention as well using different optimized parameters to insert the DNA template together with the vector into the host cells.

The following examples are intended to further illustrate the invention, without any intent for the invention to be limited to the specific embodiments described therein.

Example 1

*Chlorella vulgaris* UMACC 001 culture was obtained from the University of Malaya Algae Collection (UMACC).

The microalga sample was cultured and maintained in the Algae Research Laboratory, Institute of Graduate Studies, University of Malaya. *C. vulgaris* was cultured in Bold's Basal Medium (BBM) (Nichols and Bold, 1965) at 25° C. and 282.45 µmol·s$^{-1}$m$^{-2}$ (Phang and Chu, 2004).

Example 2

The synthetic gene VP28 was assembled from synthetic oligonucleotides and cloned into plasmid pGA4 (ampR). The plasmid DNA was purified from transformed bacteria and concentration was determined by UV spectroscopy. The target gene was cloned into the BamHI and PstI site of pSVβ-gal to construct the pSV40WSSV vector. Transformation was carried out in *E. coli* Top 10 using the calcium chloride heat-shock method. This vector carries an ampicilin resistant marker and cell selection can be done using blue-white colony screening. The *E. coli* harboring the pSVβ-gal with the VP28 gene was further verified by restriction digestion and sequencing. The target gene was cloned into the lac Y region of pSVβ-gal thus creating a fusion peptide with the size of 42.5 kDa.

The partial VP28 gene was designed with nucleotide sequence optimized for expression. This gene is without the N-terminal hydrophobic region [Δ1-29] of the VP28 coat protein. The peptide region was designed based on Jeroen et al., 2004. The similarity index based on Martinez (1983)/Needleman and Wunsch (1970) DNA alignment is 68%. The translation map for native VP28 gene is shown in FIG. 1 while FIG. 2 shows the codon optimized VP28 gene.

Example 3

The gold particles (Bio-Rad Laboratories, USA) sized 1.0 µm were coated with the pSV40WSSV vector containing the VP28 gene. Fifty microliters of gold particle solution (60 mg mL$^{-1}$) was mixed with 2 µL of a plasmid DNA solution (1 µL µg$^{-1}$), 50 µL of 2.5 M CaCl$_2$, and 20 µL of 0.1M spermidine. The mixture was vortexed and centrifuged to remove the supernatant. The remaining gold particles with plasmid DNA were resuspended in 250 µL 100% Ethanol and vortexed briefly for 10 s. Finally, 10 µL of gold-DNA particle was layered on a macrocarrier for bombardment. *C. vulgaris* at a mid-log phase were bombarded using Bio-Rad PDS-1000/He Biolistic Particle Delivery System (Bio-Rad Laboratories, USA) at rupture disc pressure of 900 psi and at a distance of 9 cm. The bombarded and non-bombarded (control) *C. vulgaris* cultures were kept in BBM medium in the dark for two days before culturing into BBM agar plates.

Example 4

Once the single colonies were visible as green colored clonal colonies, they were cultured in BBM medium separately until they reached exponential phase (OD$_{620\ nm}$=0.2), which was normally on the fourth day. One hundred milliliters of *Chlorella vulgaris* (OD$_{620\ nm}$=0.2) was harvested by centrifugation at 10,000 rpm for 10 min at room temperature. The total DNA was lysed in 550 µL lysis buffer (0.1 M Tris-HCL, 0.05 M EDTA, 0.5 M NaCl and 1% BME) and homogenized by using a mortar and pestle for 3 min. Three microliters of RNase A (10 mg mL-$^{1}$) and 35 µL of 20% SDS were added to the lysate and the microcentrifuge tube was inverted for five times before incubating at 65° C. for 1 hr. The protein was precipitated with 170 µL 5 M KAc and the microcentrifuge tube was inverted slowly for five times before incubating again in ice for 20 min. Then, 600 µL of chloroform:isoamyl (24:1) was added to eliminate the protein and the microcentrifuge tube was inverted for five times until the contents were well mixed. The mixture was centrifuged at 10,000 rpm at 4° C. for 10 min. The supernatant that contained the DNA was transferred into a clean microcentrifuge tube containing 500 µL of chilled isopropanol. The solution was gently mixed by inversion until thread-like strands of DNA formed a visible mass followed by centrifugation at 10,000 rpm for 10 min at 4° C. The supernatant was decanted and the pellet was washed with 500 µL of 70% ethanol at room temperature by gentle inversion. The DNA was recovered by centrifugation at 10,000 rpm for 5 min at 4° C. The ethanol was carefully aspirated by using a micropipette before inverting the tube onto clean absorbent paper and air-drying the pellet for 30 min. Then, the DNA was dissolved in 50 µL TE (pH 8.0) at 65° C. The DNA was stored at −20° C. until used.

The quantity and purity of the genomic DNA were determined by a biophotometer (Eppendorf, Germany) at OD$_{260\ nm}$ and OD$_{280\ nm}$. The ratio between the absorbance values at 260 nm and 280 nm gave an estimate of the DNA purity. The quality and integrity of the DNA sample were also verified with 1.0% (w/v) agarose gel electrophoresis in 1×TAE buffer at 90V for 30 min. The genomic bands were viewed and photographed using AlphaImager™ 2200 (Alpha Innotech Corporation, USA).

Genomic DNA was extracted from transformed strains and untransformed strain of *Chlorella* UMACC 001 when cultures were at 6$^{th}$ generation (FIG. 3) based on specific growth rate of UMACC 001 as ranging from 0.22 to 0.30 per day. The purity of DNA obtained range from 1.80 to 2.00.

Example 5

Figure 4:
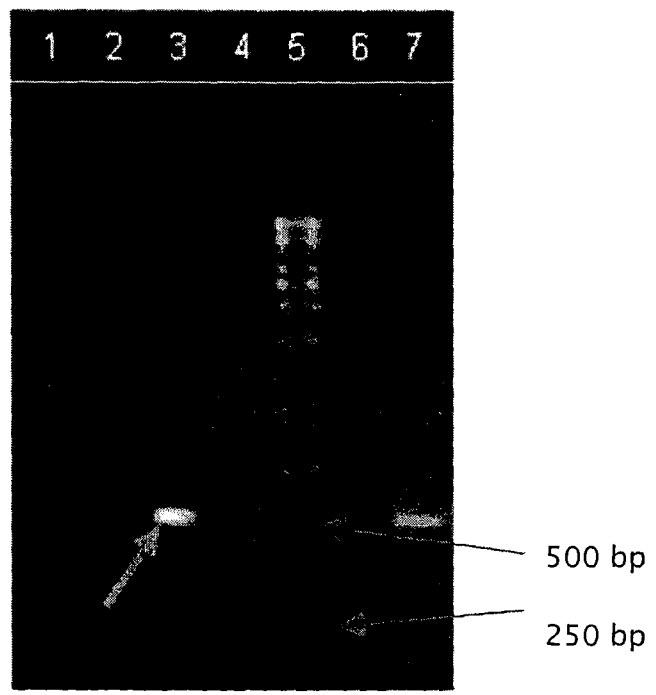
FIG. 4 shows results of the putative transformed strains (6$^{th}$ generation) which were selected by PCR analysis using primers that amplified the WSSV gene where Lane 1: PCR analysis conducted with DNA extracted from transformed *Chlorella* strain 1, WSSV1; Lane 2: PCR analysis conducted with DNA extracted from transformed *Chlorella* strain 2, WSSV2; Lane 3: PCR analysis conducted with DNA extracted from transformed *Chlorella* strain 3, WSSV3; Lane 4: PCR analysis conducted with DNA extracted from untransformed *Chlorella* strain 1, UTI; Lane 5: 1 kb DNA marker; Lane 6: PCR analysis conducted without DNA template (negative control); and Lane 7: PCR analysis conducted with the plasmid construct VP28 (positive control)
Figure 5:
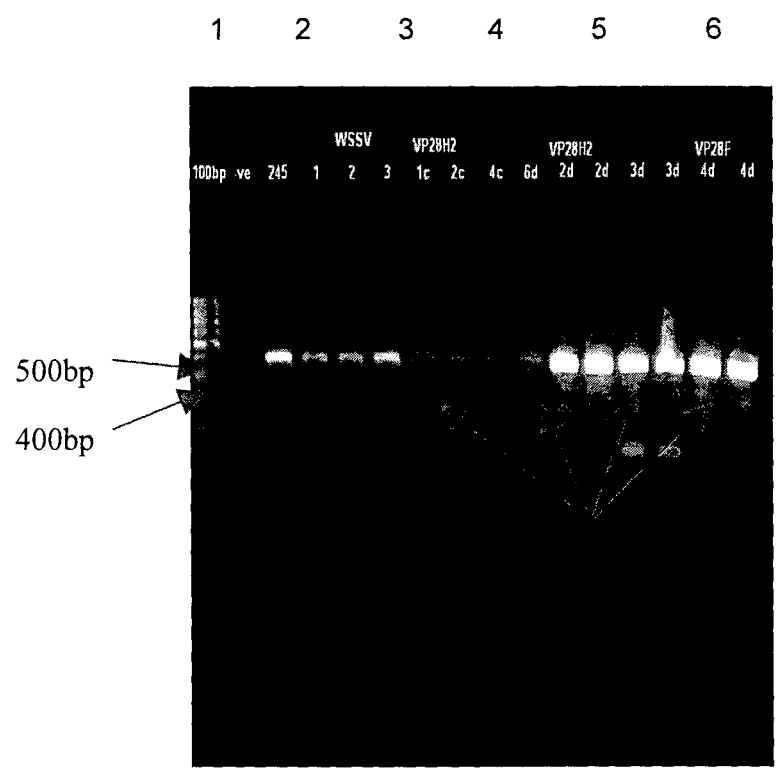
FIG. 5 shows results of a PCR analysis conducted for DNA extracted from transformed *Chlorella* that Lane 1: 100 bp DNA marker; Lane 2: PCR analysis without any DNA template (negative control); Lane 3: PCR analysis of plasmid VP28-positive control; Lane 4, 5, 6: PCR analysis of DNA extracted from WSSV samples at 90$^{th}$ generation, namely WSSV1, WSSV2, WSSV3, respectively.
Figure 7A:
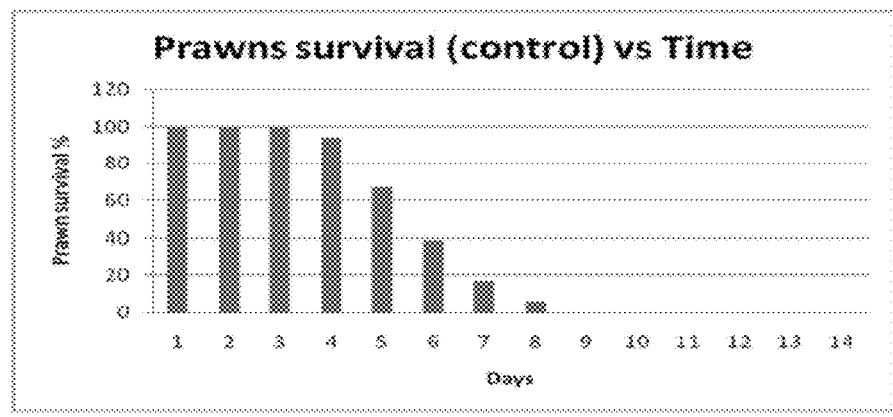
FIGS. 7a, 7b, and 7c are histograms showing results obtained from a live viral challenge experiment on prawn fed with transformed algae as an oral vaccine.
Figure 7B:
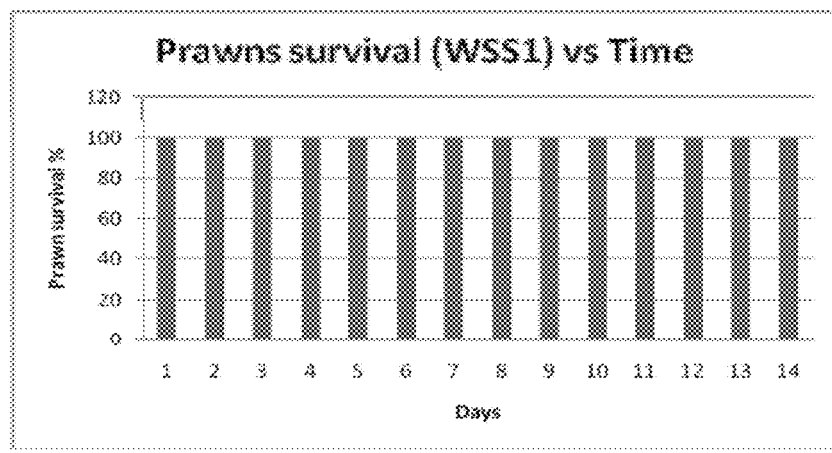
Figure 7C:
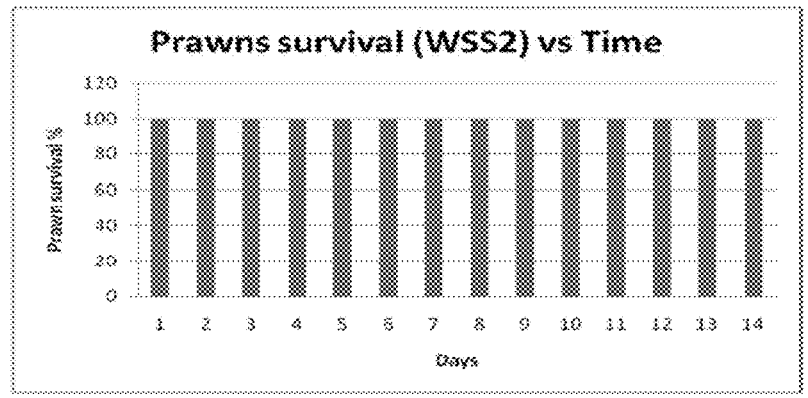

Two pairs of PCR primers were synthesized by Bio Basic Inc. (Malaysia). Partial VP28 gene fragment (573 bp) was amplified by specific primers: 5'-GCC GAA TTC GGA TCC CAT AAT ACT GTT AC-3' (i.e., SEQ. ID NO. 3) and 5'-GCC AAG CTT CTC AGT CTC AGT TCC AGA AT-3' (i.e., SEQ. ID NO. 4). The 25 µL PCR reaction consisted of 2.5 µL, 10×PCR buffer, 0.5 µL, MgCl$_2$ (100 mM), 0.4 µL, dNTP mix (10 mM) (Bioron, Germany), 1 µL forward primer (10 µM), 1 µL, reverse primer (10 µM), 2U Taq DNA Polymerase (Bioron, Germany), 1 µL genomic DNA (0.5 ng/µL) and 18.2 µL, sterile deionized water. The PCR conditions were performed as follows: 5 min at 94° C. for pre-denaturation, 1 min at 94° C. to denature the double stranded DNA strand, 1 min at 55° C. to anneal the DNA and 2 min at 72° C. to extend the PCR amplified product. The denaturation, annealing and extension steps were repeated for 35 cycles. This was followed by a final extension at 72° C. for 10 min. The PCR products were analyzed with 1.0% (w/v) agarose gel electrophoresis in 1×TAE buffer at 90V for 30 min and viewed using AlphaImager™ 2200 (Alpha Innotech Corporation, USA). As shown in FIG. 4, putative transformed strains (colonies) were selected by PCR analysis using primers that amplified the WSSV gene (573 bp). Then, the PCR amplified bands were excised from the gel for DNA sequencing.

The DNA fragments from PCR were purified from the agarose gel using the QIAquick Gel Extraction Kit (Qiagen, Germany) according to supplier's protocol. Fifty microliters of Buffer EB was applied to the column to elute the DNA and centrifuged at 10,000 rpm for 1 min at room temperature. Finally, the eluted DNA was sequenced using the same primers (5'-GCC GAA TTC GGA TCC CAT AAT ACT GTT AC-3' (i.e., SEQ. ID NO. 3) and 5'-GCC AAG CTT CTC AGT CTC AGT TCC AGA AT-3') (i.e., SEQ. ID NO. 4). The obtained sequence was compared with the sequence of VP28 which was incorporated into the construct to confirm that the amplified PCR fragment was the desired VP28 gene. Sequence analysis was conducted using ClustalW.

PCR analysis of partial VP28 gene fragment using primers set (5'-CCC TGT TAC TGC TGA AGT TGG-3' (i.e., SEQ. ID NO. 5) and 5'-TGT TGC AGC AAT AGG AGC AC-3' (i.e., SEQ. ID NO. 6)) was also conducted for both transformed (WSSV1, WSSV2, and WSSV3) and non-transformed *Chlorella* harvested at $90^{th}$ generation (450 days after transformation) which generated a desired band of approximately 391 bp. The 25 μL PCR reaction consisted of 5.0 μL 5× GoTaq™ reaction buffer, 1.5 μL $MgCl_2$ (25 mM), 0.5 μL dNTP mix (10 mM), 0.5 μL forward primer (10 μM), 0.5 μL reverse primer (10 μM), 1U GoTaq™ DNA Polymerase (Promega, USA), 1 μL genomic DNA (1.0 μg/μL) and 15.8 μL sterile deionized water. The PCR conditions were performed as follows: 5 min at 94° C. for pre-denaturation, a total of 40 cycles of 1 min at 94° C. to denature the double stranded DNA strand, 1 min at 53° C. to anneal the DNA and 1 min at 72° C. to extend the PCR amplified product. FIG. 5 shows that the VP28 gene was still detected from the DNA extracted from culture of transformed *Chlorella* at $90^{th}$ generation.

Example 6

Genomic DNA of the transformed positive clones ($6^{th}$ cell generation) and untransformed DNA were digested for three days with restriction enzymes, BamHI and PstI (Promega, USA) which cut the VP 28 gene out from the construct, pSV40WSSV to give a band size of 573 bp. The digested products were separated by electrophoresing on 0.8% (w/v) agarose gel in 1×TAE at 90V for 30 min and viewed using AlphaImager™ 2200 (Alpha Innotech Corporation, USA).

After DNA fractionation, the gel was trimmed to remove unused areas of the gel. The DNA was depurinated in 0.2 M HCl for 30 min. Then, the DNA was denatured by soaking the gel in Denaturation Solution (1.5 M NaCl, 0.5 M NaOH) for 30 min with constant agitation. Then, the gel was briefly rinsed in deionized water, followed by soaking of the gel in Neutralization Buffer (0.5 M Tris, 1.5 M NaCl, pH 7.5) for 30 min with constant agitation. Meanwhile, charged nylon membrane, Hybond N+ (Amersham, U.K) was soaked in deionized water for 30 sec prior to soaking it in Nucleic Acid Transfer Buffer, 20×SSC (0.3M Tri-sodium citrate, 3 M NaCl) for 5 min.

A 3 mm filter paper (Whatman, USA) was placed on a plastic platform in a blotting reservoir that was wider and longer than the gel. The ends of the filter paper were left to drape over the edges of the platform. The reservoir was filled with Nucleic Acid Transfer Buffer until the filter paper on the plastic platform became thoroughly wet, before smoothing out the air bubbles with a glass pipette. Then, the gel was removed from the solution and inverted so that its underside was at the uppermost and the gel was placed on the support. The top of the gel was moistened with Nucleic Acid Transfer Buffer so that the moistened membrane could be placed on the gel. Two pieces of 3 mm filter paper (Whatman, USA) were wet in Nucleic Acid Transfer Buffer and placed on the wet membrane avoiding any air bubble formation.

Finally, paper towels (five to eight centimeters high) were cut and placed on the filter paper A weight was put on the top of paper towel. The transfer of DNA was allowed for 24 hours. Then, the membrane was soaked in Neutralization Buffer for 20 min prior to hybridization. The target DNA was detected using the North2South Biotin Chemiluminescent Kit (Pierce Biotechnology, USA). The probe that was used for detection was the PCR product of pSV40WSSV amplified (573 bp) using the specific primers (as in reported in the PCR analysis). X-ray film was exposed to the membrane and a band (573 bp) was detected as expected. This indicated the integration of the WSSV gene into the host genome (FIG. 6).

REFERENCE

1. Jeroen, W., Carolina, C. C., Just, M. V. and Mariëlle C. W. van Hulten. (2004). Protection of *Penaeus monodon* against White Spot Syndrom Virus by Oral Vaccination. *Journal of Virology,* 2057-2061.
2. Martinez, H. M. (1983). An Efficient Method for Finding DNA Repeats in Molecular Sequences. *Nucleic Acids Research,* 11: 4629-4634.
3. Needleman, S. B. and C. D. Wunsch (1970). A General Method Applicable to The Search for the Similarities in Amino Acid Sequence of Two Proteins. *Journal of Molecular Biology,* 48: 443-453.
4. Nichols, H. W. and Bold, H. C. (1965). *Trichosarcina polymorpha* gen. et sp. nov. *Journal of Phycology* 1: 34-38.
5. Phang, S. M. and Chu, W. L. (2004). The University of Malaya Algae Culture Collection (UMACC) and potential applications of a unique *Chlorella* from the collection. *Japanese Journal of Phycology.,* 52: 221-224.

The invention claimed is:

1. A method of producing an agent capable of eliciting an immune response against White Spot Syndrome Baculovirus complex in an animal of the Penaeidae family upon ingestion of the agent, comprising the steps of;
   introducing a vector containing a nucleic acid sequence encoding SEQ ID NO: 1 into an alga to transform the algae; and
   cultivating the transformed algae to express modified VP28 peptides according to the nucleic acid sequence encoding SEQ ID NO: 1 to obtain the agent.

2. The method of claim 1, wherein the vector is a pSV-beta-galactosidase control vector.

3. The method of claim 1, wherein the introducing step is performed using particle bombardment.

4. The method of claim 1, wherein the algae is *Chlorella vulgaris*.

5. The method of claim 1, wherein the expressed modified VP28 peptides are free of the first 29 amino acids at an N-terminal of the unmodified peptides.

6. An agent operable to elicit an immune response against White Spot Syndrome Baculovirus complex in crustaceans of the Penaeidae family upon ingestion of the agent produced according to claim 1.

* * * * *

SEQUENCE LISTING

```
<160> NUMBER OF SEQ ID NOS: 7

<210> SEQ ID NO 1
<211> LENGTH: 198
<212> TYPE: PRT
<213> ORGANISM: ARTIFICIAL
<220> FEATURE:
<223> OTHER INFORMATION: SYNTHETIC CONSTRUCT

<400> SEQUENCE: 1

Gly Glu Leu Gly Thr Ala Thr Gly Ser His Asn Thr Val Thr Lys Thr
1               5                   10                  15

Ile Glu Thr His Thr Asp Asn Ile Glu Thr Asn Met Asp Glu Asn Leu
            20                  25                  30
```

Arg Ile Pro Val Thr Ala Glu Val Gly Ser Gly Tyr Phe Lys Met Thr
            35                  40                  45

Asp Val Ser Phe Asp Ser Asp Thr Leu Gly Lys Ile Lys Ile Arg Asn
 50                  55                  60

Gly Lys Ser Asp Ala Gln Met Lys Glu Glu Asp Ala Asp Leu Val Ile
 65                  70                  75                  80

Thr Pro Val Glu Gly Arg Ala Leu Glu Val Thr Val Gly Gln Asn Leu
                 85                  90                  95

Thr Phe Glu Gly Thr Phe Lys Val Trp Asn Thr Ser Arg Lys Ile
            100                 105                 110

Asn Ile Thr Gly Met Gln Met Val Pro Lys Ile Asn Pro Ser Lys Ala
            115                 120                 125

Phe Val Gly Ser Ser Asn Thr Ser Ser Phe Thr Pro Val Ser Ile Asp
            130                 135                 140

Glu Asp Glu Val Gly Thr Phe Val Cys Gly Thr Thr Phe Gly Ala Pro
145                 150                 155                 160

Ile Ala Ala Thr Ala Gly Gly Asn Leu Phe Asp Met Tyr Val His Val
                165                 170                 175

Thr Tyr Ser Gly Thr Glu Thr Glu Leu Gln Thr Lys Leu Ala Glu Phe
            180                 185                 190

Glu Leu Gln Leu Leu Phe
            195

<210> SEQ ID NO 2
<211> LENGTH: 594
<212> TYPE: DNA
<213> ORGANISM: ARTIFICIAL
<220> FEATURE:
<223> OTHER INFORMATION: SYNTHETIC CONSTRUCT

<400> SEQUENCE: 2
ggcgaattgg gtaccgctac tggatcccat aatactgtta ctaagactat tgaaactcat    60
actgataata ttgaaactaa tatggatgag aacctcagaa tccctgttac tgctgaagtt   120
ggatctggat acttcaagat gactgatgtg tctttcgatt ctgatactct cggaaagatc   180
aagatcagaa acggaaagtc tgatgctcag atgaaggaag aggatgctga tctcgttatc   240
actcctgttg agggaagagc tttggaagtt actgtgggac aaaatcttac tttcgaggga   300
actttcaaag tgtggaacaa cacttctaga aagatcaaca tcactggaat gcaaatggtg   360
cctaagatca acccttctaa ggctttcgtt ggttcttcta acacttcttc tttcacacct   420
gtgtctatcg atgaggatga agtgggaact ttcgtgtgtg gaactacttt cggtgctcct   480
attgctgcaa cagcaggtgg aaacctcttc gatatgtacg tgcacgtgac ttattctgga   540
actgagactg agctgcagac caagcttgcc gaattcgagc tccagctttt gttc          594

<210> SEQ ID NO 3
<211> LENGTH: 29
<212> TYPE: DNA
<213> ORGANISM: ARTIFICIAL
<220> FEATURE:
<223> OTHER INFORMATION: PRIMER

<400> SEQUENCE: 3
gccgaattcg gatcccataa tactgttac                                       29

<210> SEQ ID NO 4
<211> LENGTH: 29
<212> TYPE: DNA

```
<213> ORGANISM: ARTIFICIAL
<220> FEATURE:
<223> OTHER INFORMATION: PRIMER

<400> SEQUENCE: 4
gccaagcttc tcagtctcag ttccagaat                              29

<210> SEQ ID NO 5
<211> LENGTH: 21
<212> TYPE: DNA
<213> ORGANISM: ARTIFICIAL
<220> FEATURE:
<223> OTHER INFORMATION: PRIMER

<400> SEQUENCE: 5
ccctgttact gctgaagttg g                                      21

<210> SEQ ID NO 6
<211> LENGTH: 20
<212> TYPE: DNA
<213> ORGANISM: ARTIFICIAL
<220> FEATURE:
<223> OTHER INFORMATION: PRIMER

<400> SEQUENCE: 6
tgttgcagca ataggagcac                                        20

<210> SEQ ID NO 7
<211> LENGTH: 204
<212> TYPE: PRT
<213> ORGANISM: WHITE SPOT SYNDROME VIRUS

<400> SEQUENCE: 7
```

Met Asp Leu Ser Phe Thr Leu Ser Val Val Ser Ala Ile Leu Ala Ile
1               5                   10                  15

Thr Ala Val Ile Ala Val Phe Ile Val Ile Phe Arg Tyr His Asn Thr
            20                  25                  30

Val Thr Lys Thr Ile Glu Thr His Thr Asp Asn Ile Glu Thr Asn Met
        35                  40                  45

Asp Glu Asn Leu Arg Ile Pro Val Thr Ala Glu Val Gly Ser Gly Tyr
    50                  55                  60

Phe Lys Met Thr Asp Val Ser Phe Asp Ser Asp Thr Leu Gly Lys Ile
65                  70                  75                  80

Lys Ile Arg Asn Gly Lys Ser Asp Ala Gln Met Lys Glu Glu Asp Ala
                85                  90                  95

Asp Leu Val Ile Thr Pro Val Glu Gly Arg Ala Leu Glu Val Thr Val
            100                 105                 110

Gly Gln Asn Leu Thr Phe Glu Gly Thr Phe Lys Val Trp Asn Asn Thr
        115                 120                 125

Ser Arg Lys Ile Asn Ile Thr Gly Met Gln Met Val Pro Lys Ile Asn
    130                 135                 140

Pro Ser Lys Ala Phe Val Gly Ser Ser Asn Thr Ser Ser Phe Thr Pro
145                 150                 155                 160

Val Ser Ile Asp Glu Asp Glu Val Gly Thr Phe Val Cys Gly Thr Thr
                165                 170                 175

Phe Gly Ala Pro Ile Ala Ala Thr Ala Gly Gly Asn Leu Phe Asp Met
            180                 185                 190

Tyr Val His Val Thr Tyr Ser Gly Thr Glu Thr Glu
        195                 200